United States Patent [19]

Rodriguez

[11] Patent Number: 4,514,318

[45] Date of Patent: Apr. 30, 1985

[54] STABILIZING POLYSACCHARIDE-THICKENED AQUEOUS MEDIUM AND STABLE AQUEOUS GEL

[75] Inventor: Philip A. B. Rodriguez, Mont-St.-Hilaire, Canada

[73] Assignee: C-I-L Inc., North York, Canada

[21] Appl. No.: 580,188

[22] Filed: Feb. 15, 1984

[30] Foreign Application Priority Data

Apr. 14, 1983 [CA] Canada ................................ 425914

[51] Int. Cl.$^3$ .......................... B01J 13/00; C08L 3/02; C08L 5/00
[52] U.S. Cl. .................................... 252/315.3; 106/25; 106/208; 149/108.8; 426/573
[58] Field of Search .................. 252/315.3; 149/108.8; 106/208; 424/361

[56] References Cited

U.S. PATENT DOCUMENTS

| | | | |
|---|---|---|---|
| 2,870,059 | 1/1959 | Williams et al. | 252/315.3 X |
| 3,084,057 | 4/1963 | Jordan | 106/208 X |
| 3,146,200 | 8/1964 | Goldstein et al. | 106/208 X |
| 3,251,781 | 5/1966 | Jordan | 252/315.3 |

OTHER PUBLICATIONS

The Condensed Chemical Dictionary, 6th Edition, Edited by Rose et al., Reinhold Publ. Corp., New York, 1961, p. 1122.

Primary Examiner—Richard D. Lovering
Attorney, Agent, or Firm—Donald G. Ballantyne

[57] ABSTRACT

A means is provided for stabilizing polysaccharide-thickened aqueous solutions by including in the thickened solution from 0.01% to 1% w/w of a thiuram sulphide or thiomorpholine compound as stabilizer. These stabilizers provide improved resistance against breakdown of the gels and separation of the gel ingredients particularly when the gels are exposed to elevated temperatures. The invention has application in the fields of paints, pharmaceuticals, printing, explosives or wherever polysaccharide-thickened aqueous solutions are employed.

5 Claims, No Drawings

STABILIZING POLYSACCHARIDE-THICKENED AQUEOUS MEDIUM AND STABLE AQUEOUS GEL

This invention relates to aqueous solutions or dispersions which are thickened or gelled by means of water soluble polysaccharides. In particular, the invention provides polysaccharide-thickened aqueous solutions which have improved stability, especially at elevated temperatures.

The use of polysaccharides for thickening or gelling purposes is widely practised. When polysaccharides are dispersed in an aqueous medium, a hydrophilic colloid results which is particularly viscous in nature. Such viscous solutions, gels or pastes have found general use as thickeners in a wide range of applications, for example, paints, textiles, food products, printing inks, pharmaceuticals and explosives.

In many applications, the stability of polysaccharide-thickened aqueous solutions has been difficult to maintain over long time periods, especially when the gels are exposed to above-ambient temperatures. This loss of stability is evident in a breakdown of the gels, separation of the ingredients, or in syneresis. The prior art describes various methods for stabilizing the viscosity of these thickened solutions. These methods include, for example, the heating of the dry polysaccharide prior to dissolution, treating the polysaccharide with various chemicals, such as, ethylene glycol, $SO_2$, or with various acids. In U.S. Pat. No. 3,007,879, the inclusion in the solution of an iron inactivating agent is suggested, e.g., citric, oxalic and tartaric acids. In Canadian Pat. No. 658,527, the addition of a water soluble thio-organic compound is proposed. U.S. Pat No. 3,251,781 advocates the inclusion of oxides and sulphides of selected metals in water solutions of galactomannan gums. In U.S. Pat. Nos. 3,202,556, 3,301,723, 3,445,305 and 3,485,686, the use of various crosslinking or chelating agents is disclosed to stabilize galactomannan-water mixtures.

While all of the above-noted discoveries are meritorious, none is completely successful as a stabilization technique, particularly when the polysaccharide-thickened aqueous solution is exposed to above ambient temperatures for any length of time.

According to the present invention, the stability of polysaccharide-thickened aqueous solutions can be markedly improved by including in such solutions a water-insoluble, sulphur-containing compound in which a sulphur atom is bonded to a carbon atom, a nitrogen atom or to another sulphur atom. Such compounds, for example, thiuram sulphides, thiomorpholines and the like, are exemplified by the structures below:

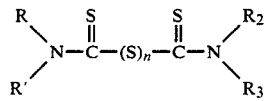

where
n = 1 or 2

R = R₁ = R₂ = R₃ = CH₃, C₂H₅, C₃H₇, C₄H₉, or

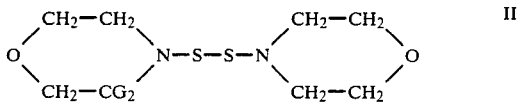

Particularly preferred are the following commercially available compounds:
Tetrabutyl thiuram disulphide
Tetraethyl thiuram disulphide
Tetramethyl thiuram disulphide
Dithiomorpholine
Tetramethyl thiuram monosulphide.

These stabilizers are in the form of a dry powder or an oily liquid (tetrabutyl thiuram disulphide).

Typical water soluble polysaccharide thickeners which may be stabilized by the method of the invention include, for example, gum arabic, agar-agar, Irish moss, locust bean, tamerind, psyllium, xanthan or guar gums, starches and hydroxyethyl cellulose.

The polysaccharide-thickened aqueous solutions stabilized by the method of the present invention will normally contain from 0.05% to about 10% of polysaccharide-thickening agent, based on the total weight of water and thickener. The stabilizer comprises from 0.01% to about 1%, preferably, from 0.03% to 0.5% by weight of the total composition and will generally be in proportion to the amount of thickener present.

The thickened aqueous solution may be stabilized either by blending the stabilizer and polysaccharide thickener prior to addition to the water or the stabilizer may be added with vigorous stirring to an already thickened or to an unthickened aqueous medium. Because of the substantially insoluble nature of the stabilizer, adequate mixing is required to obtain optimum results.

The following Examples will further describe the present invention.

EXAMPLES 1-7

A typical test aqueous salt solution was prepared similar to those employed in many slurry explosives or pharmaceutical formulations as follows:

| | |
|---|---|
| 660 parts by wt. | ammonium nitrate (tech. grade) |
| 133.5 parts by wt. | sodium nitrate (tech. grade) |
| 1.5 parts by wt. | zinc nitrate (tech. grade) |
| 205 parts by wt. | water (steam distillate) (tech. grade) |

Seven measured proportions of the test solution in glass beakers were thickened by adding 0.67% by wt. of chemically unmodified guar gum (JaGUAR 170, Reg. T. M. Celanese Corp.). To the separate thickened proportions of test solution was added 0.1% by wt. of different stabilizers. The apparent viscosity of the thickened and stabilized solution as measured as made and after storage for 100 hours at 60° C. Viscosity was measured using a Brookfield HBT instrument with spindle No. 1 at rpm of 0.5, 1, 2.5 and 5. The results at 0.5 and 1.0 rpm were extrapolated to zero rmp to give a "zero shear" apparent viscosity. (The results at 2.5 and 5 rpm can be used to check the accuracy of the 0.5 rpm apparent viscosity). The resuts are shown in Table I below.

TABLE I

Stabilization of the Viscosity of an Unmodified (Chemically) Guar JaGUAR 170 ® (Celanese Corp.) Guar Level 0.67% wt/wt

| EX. | STABILIZER | LEVEL WT/WT | pH | INITIAL VISCOSITY | VISCOSITY 100 HRS. @ 60° C. | HALF LIFE (HRS)* | HALF LIFE WITHOUT STABILIZER (HRS) |
|---|---|---|---|---|---|---|---|
| 1 | Tetrabutyl thiuram Disulphide ButylTUADS ® | 0.1% | 4.2 | 35,000 | 10,000 | 63 | 40 |
| 2 | Tetraethyl Thiuram Disulphide EthylTUADS ® | 0.1% | 4.5 | 44,000 | 14,500 | 63 | 48 |
| 3 | Tetramethyl Thiuram Disulphide Methyl-TUADS ® Tread Grade | 0.1% | 4.5 | 35,000 | 17,000 | 103 | 48 |
| 4 | Dithiomorpholine Sulfasan R ® | 0.1% | 4.3 | 13,000 | 4,900 | 72 | 40 |
| 5 | Tetramethyl Thiuram Disulphide Thiurad ® | 0.1% | 4.1 | 31,000 | 9,000 | 55 | 40 |
| 6 | Tetramethyl Thiuram Monosulphide Monothiurad ® | 0.1% | 4.2 | 30,500 | 9,800 | 60 | 40 |
| 7 | None | — | 4.2 | 35,000 | 7,000 | — | 40 | pH as measured by Fisher Accumot (Reg. T.M.) pH meter Model 600
*Time taken for viscosity to drop to half its initial value.

As can be seen from Table I, the composition sample No. 7 devoid of stabilizer exhibited a substantially sharper drop in viscosity after storage than all other samples. Also, the viscosity half life (time for viscosity to drop to half its initial value) was substantially improved in presence of the stabilizer.

EXAMPLES 8-12

A series of salt-containing aqueous test solutions were prepared in glass beakers as in Examples 1-7. A portion of a known stabilizer was added to separate samples of the solution and the viscosity measured as made and after 100 hours storage at 60° C. The results are tabulated in Table II below.

TABLE II

Known Stabilizers

| EX. | GUAR | LEVEL WT/WT | STABILIZER | LEVEL WT/WT | INITIAL VISCOSITY | VISCOSITY 100 HRS @ 60° C. | pH | HALF LIFE (HRS) | HALF LIFE WITHOUT STAB (HRS) |
|---|---|---|---|---|---|---|---|---|---|
| 8 | J170* | 0.67% | Thiourea | 0.1% | 32,000 | 7,400 | 4.1 | 48 | 40 |
| 9 | J170 | 0.67% | Sodium Thiosulphate | 0.1% | 46,000 | 12,600 | 4.2 | 54 | 40 |
| 10 | J170 | 0.67% | Ethylene Glycol | 1.0% | 12,000 | 2,000 | 4.2 | 45-50 | 40 |
| 11 | J170 | 0.67% | Sodium Sulphite | 0.1% | 26,000 | 7,200 | 4.4 | 54 | 44 |
| 12 | J170 | 0.67% | None | — | 35,000 | 7,000 | 4.2 | — | 40 |

Adjustment of the pH was necessary
*JaGUAR 170 (Reg. T.M. Celanese Corp.)

The results in Table II show that the use of known stabilizer was less efficient in maintaining stability during storage then were the stabilizers of the present invention. (Table I). Also, the viscosity half life was generally less using known stabilizers.

EXAMPLES 13-18

Various quantities of tetramethyl thiuram disulphide were added to separate guar-thickened samples of test solution (as per Examples 1-7) and the viscosity measured as made and after 50 hours storage at 60° C. The results are tabulated in Table III below.

TABLE III

Effect of Tetramethyl Thiuram Disulphide Stability at pH 4.2 Using JaGUAR 170 ® as the Guar at 0.67%

| EX. | STABILIZER LEVEL WT/WT | INITIAL VISCOSITY | VISCOSITY 50 HRS @ 60° C. | HALF LIFE (HRS) | HALF LIFE WITHOUT STABILIZER (HRS) |
|---|---|---|---|---|---|
| 13 | 0.01% | 36,500 | 17,000 | 46 | 40 |
| 14 | 0.05% | 30,000 | 18,000 | 72 | 40 |
| 15 | 0.1% | 32,000 | 19,800 | 72 | 40 |
| 16 | 0.2% | 31,000 | 16,100 | 53 | 40 |
| 17 | 0.3% | 32,600 | 16,500 | 50 | 40 |
| 18 | None | 35,000 | 7,000 | — | 40 |

As will be seen from Table III, the stabilizer is effective over a relatively wide range of concentration. The larger concentrations used (Examples 16 and 17) do not necessarily provide the greatest improvement in storage stability.

EXAMPLES 19-34

A number of different polysaccharide thickeners were added to samples of test solution (as per Examples 1-7) with and without various added thiuram disulphide stabilizers. The viscosity was measured as made and after 100 hours storage at 60° C. The results are shown in Table IV below.

TABLE IV

Comparison of various polysaccharide thickeners

| EXAMPLE | THICKENER | LEVEL WT/WT | STABILIZER | LEVEL WT/WT | INTITIAL VISCOSITY | VISCOSITY 100 HRS. @ 60° C. | pH | HALF LIFE (HRS) | HALF LIFE WITHOUT STABILIZER (HRS) |
|---|---|---|---|---|---|---|---|---|---|
| 19 | JaGUAR 170 ® | 0.67% | TMT [1] | 0.1% | 35,000 | 17,000 | 4.5 | 103 | 44 |
| 20 | JaGUAR 170 | 0.67% | None | — | 35,000 | 7,000 | 4.2 | — | 44 |
| 21 | JaGUAR HP-8 ® (hydroxypropyl guar) | 0.67% | TMT | 0.1% | 17,000 | 10,700 | 4.5 | 150 | 45.5 |
| 22 | JaGUAR HP-8 (hydyroxypropyl guar) | 0.67% | None | — | 16,500 | 3,400 | 4.5 | — | 45.5 |
| 23 | NGL 8529 ® (oxidized guar) | 1.0% | TBT [2] | 0.1% | 3,900 | 1,400 | 4.3 | 65 | 44 |
| 24 | NGL 8529 (oxidized guar) | 1.0% | None | — | 3,600 | 680 | 4.3 | — | 44 |
| 25 | GALACTSOL 423 ® (oxidized guar) | 1.5% | TMT | 0.1% | 17,050 | 13,800 | 4.3 | 319 | 118 |
| 26 | GALACTSOL 423 (oxidized guar) | 1.5% | None | — | 13,600 | 7,400 | 4.3 | — | 118 |
| 27 | Tapioca | 2.0% | TMT | 0.1% | 29,000 | 13,000 | 4.1 | 90 | 61 |
| 28 | Tapioca | 2.0% | None | — | 29,500 | 9,400 | 4.1 | — | 61 |
| 29 | Psyllium gum | 2.0% | TMT | 0.1% | 29,200 | 22,000 | 5.5 | 274 | 96 |
| 30 | Psyllium gum | 2.0% | None | — | 19,600 | 8,500 | 5.5 | — | 96 |
| 31 | Pregelatinized corn starch | 5.0% | TMT | 0.1% | 8,200 [5] | 1,000 [3] | 4.1 | — | — |
| 32 | Pregelatinized corn starch | 5.0% | None | — | 12,500 [5] | 290 [3] | 4.1 | — | — |
| 33 | Xanthan gum | 2.0% | TMT | 0.1% | 605,000 | 310,000 [4] | 4.1 | 99.6 days | 88.5 days |
| 34 | Xanthan gum | 2.0% | None | — | 710,000 | 405,000 [4] | 4.1 | — | 88.5 days |

[1] Tetramethyl thiuram disulphide MethylTUAD ® Thread Grade
[2] Tetrabutyl thiuram disulphide
[3] At 19 days
[4] At 70 days
[5] Viscosity measured using a Brookfield RVT instrument with a #1 Brookfield spindle at 60° C. extrapolated to zero shear.

The results in Table IV demonstrate that the stabilizers of the invention may be employed with a wide range of water-soluble polysaccharide thickeners.

I claim:

1. A method of stabilizing a polysaccharide-thickened aqueous medium which comprises adding to a polysaccharide/water mixture from 0.01% to 1% by weight of the total composition of a water-insoluble, oxidizable, sulphur-containing compound selected from the group consisting of tetrabutyl thiuram disulphide, tetraethyl thiuram disulphide, tetramethyl thiuram disulphide, dithiomorpholine and tetramethyl thiuram monosulphide.

2. A method as claimed in claim 1 wherein the polysaccharide-thickened aqueous medium is an aqueous salt solution.

3. A method as claimed in claim 1 wherein the polysaccharide thickener is selected from the group consisting of modified and unmodified guar, tapioca, psyllium, xanthan and corn starch.

4. A stable aqueous gel comprising a mixture of water and a polysaccharide thickener and from 0.01% to 1% by weight of the total composition of a stabilizer comprising a water-insoluble, oxidizable, sulphur-containing compound selected from the group consisting of tetrabutyl thiuram disulphide, tetraethyl thiuram disulphide, tetramethyl thiuram disulphide, dithiomorpholine and tetramethyl thiuram monosulphide.

5. An aqueous gel as claimed in claim 4 wherein the polysaccharide thickener is selected from the group consisting of modified and unmodified guar, tapioca, psyllium, xanthan and corn starch.

* * * * *